United States Patent [19]

Presgrove

[11] Patent Number: 4,987,784
[45] Date of Patent: Jan. 29, 1991

[54] PARTICLE SAMPLE DEVICE

[76] Inventor: Sammy B. Presgrove, 2206 Edgewood Dr., Augusta, Ga. 30904

[21] Appl. No.: 464,400

[22] Filed: Jan. 12, 1990

[51] Int. Cl.$^5$ ............................................... G01N 1/20
[52] U.S. Cl. ................................................. 73/863.52
[58] Field of Search .................. 73/863.21, 863.41, 863.51–863.58, 73/864.73

[56] References Cited

U.S. PATENT DOCUMENTS

| | | | |
|---|---|---|---|
| 3,250,128 | 5/1966 | Cassel | 73/863.51 |
| 3,260,120 | 7/1966 | Stilwell | 73/863.54 |
| 3,507,155 | 4/1970 | Segl, Jr. | 73/863.61 |
| 3,594,087 | 7/1971 | Starks et al. | 73/863.54 |

OTHER PUBLICATIONS

Minns et al., "A New Technique for Measuring the Efficiency of Particle Sampling Probes in Flowing Liquid Systems", Post Doctoral Fellow, Whiteshell Nuclear Research Establishment, Pinawa, Manitoba, R0E 1L0, Dec. 1974.

Primary Examiner—Robert Raevis

[57] ABSTRACT

A device used to obtain a representative sample of particles flowing through conduit. The device comprises an inside end of tube inserted into the bottom of said conduit with a tube particle opening facing upstream into the slurry flowing in said conduit. The outside end is attached to sample collector. As the particle slurry flows past said particle opening a small number of the particles will enter said particle opening and by gravity, fall into said sample collector.

1 Claim, 1 Drawing Sheet

PARTICLE SAMPLE DEVICE

THE FIELD OF THE INVENTION

This invention relates in general to sample devices, and in particular, sample of particles flowing in conduit.

DESCRIPTION OF RELATED ART

In the process of transferring particles, as resin, from one location to another, using the slurry mechanism, many times it is desirable to have a representative sample of the entire volume of the transferred resin.

Currently two methods are used to obtain that sample. One uses the sample plunger (U.S. Pat. No. 4,147,062) system. As the slurry flows in a conduit past the sample point, periodically a plunger piston is inserted into the conduit. The piston would then immediately be retracted with a small portion of the slurry into the sample cylinder. The sample cylinder then redirects that small portion of the slurry into a sample bomb. The fundamental problem is that when the slurry contains a variety of resin not thoroughly mixed prior to transfer, this method does not provide a representative sample. The small portion of the slurry is a discreet segment of the resin flowing passed the sample point at that moment. Each segment will be comprised of various resins. Therefore, the sample won't represent the entire volume of resin being transferred.

The other method uses a person who, when needing a sample, after transferring the resin, opens the receiving container and manually fills a beaker with the resin. This method does not provide representative sample and when sampling radioactive resin, exposes that person to undue radiation.

There are four patents which appear somewhat similar to this invention.

U.S. Pat. No. 3,595,087 (Starks)—This device samples product at a slow rate (laminar flow); the product is not transferred in a slurry with liquid; and the tube must be moveable, up and down and rotation, in order to obtain a representative sample.

U.S. Pat. No. 4,481,833 (Bajek)—This device is designed to sample the fluid in the conduit, not the particles in the fluid.

U.S. Pat. No. 3,921,458, (Logan)—This device provides a continuous sample flow of gas, not particles or product, in the conduit. It uses a sample pump to insure the flow rate in the sample tube is identical to the gas flow rate in the conduit.

U.S. Pat. No. 3,260,120, (Stilwell)—This device samples pellets only when inserted into the conduit. Normally the device will be retracted from the conduit to prevent restrictions of the low flow (laminar flow) of the pellets. And the pellets are not slurry transfered.

Whatever the precise merits, features and advantages of the above cited references, none of them achieves or fulfills the purpose of the resin sample device.

As can be seen, this invention is unique in its sampling method; that is, it is inserted at all times during a slurry transfer with no need of raising or lowering the tube and it continuously collects a small portion of the particles as the slurry passes the opening; and its design, that is, during sampling, there are no moving parts, it is inserted perpendicular to the conduit and it is designed for slurry transfer of fluid and particles (i.e., resin beads) at a high flow rate (i.e., transitional or turbulent flow).

Accordingly, it is a principle object of the present invention to provide a truly representative sample of particles, as it is transferred through conduit in the form of a slurry.

It is another principle object of the present invention to collect the sample with no moving parts of the device during sampling.

It is another principle object of the present invention to provide the representative sample regardless of the density of the slurry or the particles.

It is another principle object of the present invention, upon completion of the particle slurry transfer, to transfer the sample to an appropriate container by momentarily opening a single valve at the bottom of the sample collector.

It is another principle object of the present invention to provide a variety of sizes of sample collectors thereby providing ability of sampling any volume of particles being slurry transferred.

The forgoing objects are accomplished by providing a tube, capped or plugged on one end, with an opening in the tube wall just below the tube cap. The capped end of the tube is inserted into the bottom of the conduit used to transfer resin slurries through an appropriate fitting or union. The tube is positioned so the opening is facing into the flow of the slurry. On the free end of the tube a normally open valve is attached and on the other end of the valve, a sample collector is attached. In the bottom of the sample collector, a normally closed valve as attached.

Initially, the tube and the sample collector are filled with the fluid used to slurry transfer particles.

When a particle slurry passes the sample tube opening in the inserted tube, a very small number of particles flow into that opening.

Since no slurry fluid flows into the sample tube or the sample collector (because the sample tube and the sample collector are already full of fluid) once the particles are inside the tube, gravitation pulls the particles into the sample collector. This process continues as long as a particle slurry passes the sample tube opening.

Once the transfer is complete, an appropriate container is placed under the sample collector and the normally closed valve is momentarily opened. While the normally closed valve is open, and the inside of the slurry conduit remains pressurized with slurry fluid, the slurry fluid forces the collected particles out the bottom of the sample collector into an appropriate container.

If, for any reason, the volume of particles being transferred substantially changes, an appropriate size sample collector is exchanged with the installed one. The installed sample collector is removed (usually by merely unscrewing the sample collector from the inlet and outlet valve) and the desired size sample collector is installed in its place.

DETAILED DESCRIPTION

Figures 1, 2:
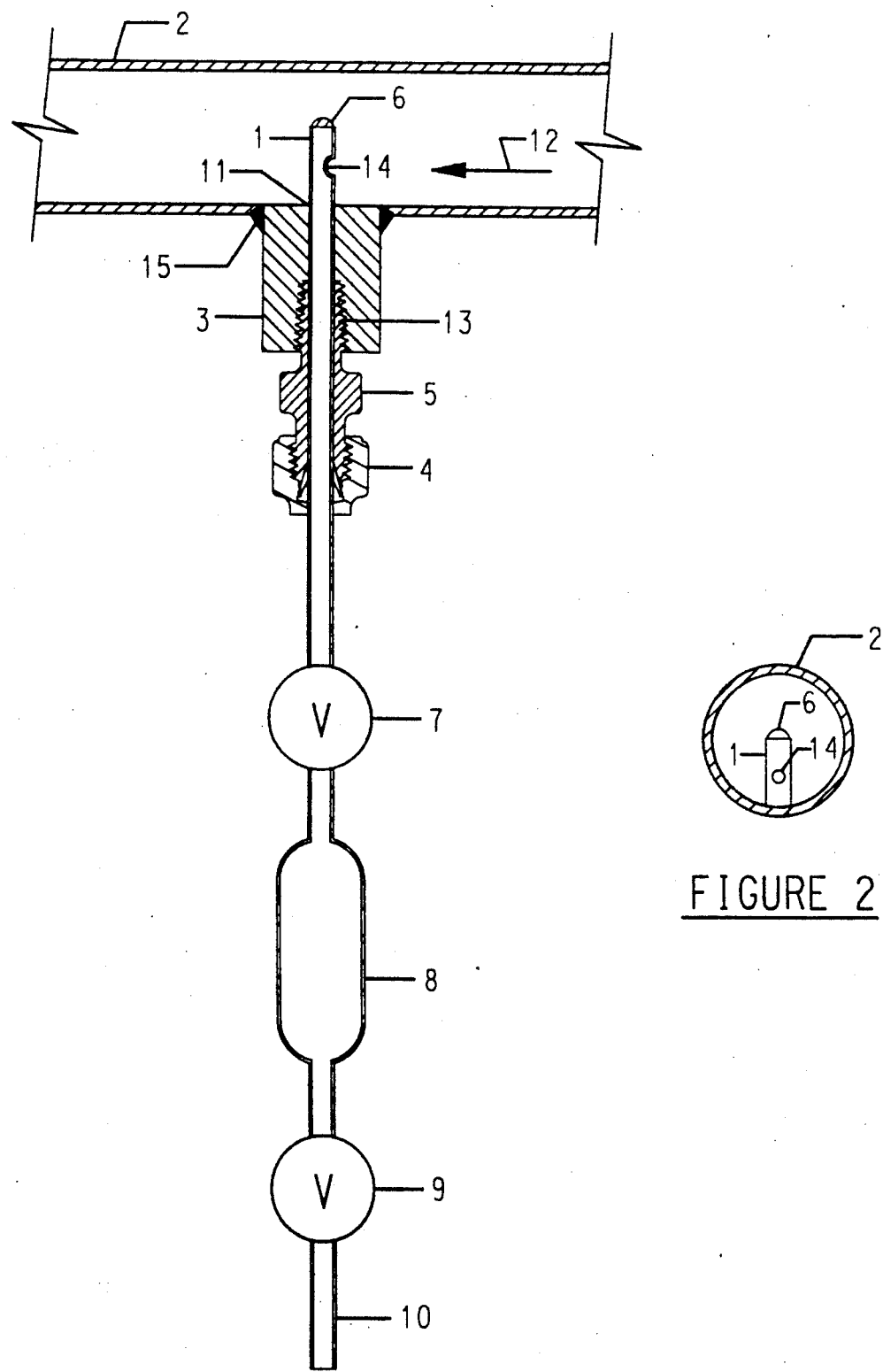
FIG. 1 is a side view of the sample device inserted into the conduit.
FIG. 2 is an enlarged, fragmentary view of the opening of the tube.

For the purposes of promoting an understanding of the principles of the invention, reference will now be made to the embodiment illustrated in the drawings and specific language will be used to describe the same. It will nevertheless be understood that no limitations of the scope of the invention is thereby intended, such alterations and further modifications in the illustrated device, and such further applications of the principles of the invention as illustrated therein being contemplated as would normally occur to one skilled in the art to which the invention relates.

FIG. 1 depicts sample tube 1 inserted in circularly conduit 2 through opening 11 in piece 3 and which is attached 15 to the conduit 2. Sample tube 1 is held in place by a compression fitting comprised of nut 4 and body 5 screwed 13 into piece 3.

In the inside or inserted portion of the sample tube 1 is plug 6 to prevent particles from entering sample tube 1 in any means other than opening 14. Opening 14 is positioned so as to face oncoming flow as shown by flow arrow 12.

On the outside end of sample tube 1 is valve 7. On the other side a valve 7 is sample collector 8. Downstream of sample collector 8 is valve 9 which may or may not have a short extension 10 on the outlet side of valve 9.

During normal operation the sample collection inlet valve 7 is open and the sample collector outlet valve 9 is closed. As a slurry of fluid and particles, such as water and resin, flows 12 passed opening 14, a small portion of the particles will enter the hollow interior of sample tube 1 through opening 14. Since sample tube 1 and sample collector 8 were filled with the fluid used to slurry the particles before the slurry transfer began, the particles will then gravitate down into sample collector 8. This process will continue until all particles are slurry transferred or until the slurry transfer is suspended.

At that time the representative sample of the particles can be transferred to an appropriate container by placing the container under sample collector 8 and opening sample collector outlet valve 9. The particles will then transfer to the container. Then close sample collector outlet valve 9.

If, for any reason, the volume of particles being transferred substantially changes, appropriate size sample collector 8 is exchanged with the existing one.

In order to exchange sample collector 8, sample collector inlet valve 7 is closed and sample collector outlet valve 9 is opened. The installed sample collector 8 is then removed (usually unscrewing the sample collector from the inlet valve 7 and the sample collector outlet valve 9) and replaced by an appropriate sample collector 8 (again by screwing the new sample collector 8 into the sample collector inlet valve 7 and the sample collector outlet valve 9).

What I claim is:

1. An apparatus for sampling particles flowing with liquid through a conduit, said apparatus comprising: a hollow tube whose longitudinal axis is positioned in a substantially vertical position and extending through a wall of the conduit, the tube having a closed upper first end and having at least one particle entry opening in a wall portion of the tube adjacent to the first end, the at least one particle entry opening facing substantially upstream of said liquid flow;

a sample collector fluidly coupled to the second end of the tube positioned outside of the conduit to receive particles;

a first valve positioned between the second end of the tube and the sample collector; and a second valve to remove particles from the sample collector;

Whereby during sampling the first valve is opened and particles enter the at least one entry opening as liquid flows passed the tube subsequently falling downward due to gravity only and into the sample collector, whereby sampled particles may be removed from the sample collector by opening the second valve so that the sampled particles may fall, and whereby the sample collector may be emptied.

* * * * *